United States Patent [19]

Thompson et al.

[11] Patent Number: 5,391,772
[45] Date of Patent: Feb. 21, 1995

[54] CONVERTING AN ALCOHOL TO AN AZIDE WITH $S_N2$ INVERSION USING A PHOSPHORYL AZIDE

[75] Inventors: Andrew S. Thompson, Mountainside; Edward J. J. Grabowski, Westfield, both of N.J.

[73] Assignee: Merck & Co., Inc., Rahway, N.J.

[21] Appl. No.: 89,315

[22] Filed: Jul. 8, 1993

[51] Int. Cl.[6] .................. C07D 307/02; C07C 247/00
[52] U.S. Cl. ........................ 549/492; 540/557;
544/336; 544/242; 544/256; 546/329; 546/176;
546/139; 548/561; 548/335.5; 548/309.7;
548/254; 548/375.1; 548/491; 548/482;
548/444; 548/247; 548/152; 548/224; 548/202;
548/235; 549/491; 549/74; 549/467; 549/49;
549/23; 552/10
[58] Field of Search ............... 552/1, 9, 10; 549/23,
549/471, 492, 469

[56] References Cited

U.S. PATENT DOCUMENTS 5,157,129 10/1992 Blacklock et al. .

OTHER PUBLICATIONS

J. Med. Chem. 1992, 35, 3745.
J. Am. Soc. 1972, 94, 679, by Mitsunobu, et al.
Org. React. 1992, 42, 335, by D. L. Hughes.
Tetrahedron Letter, 1991, 32, 7175, by C. Chen, et al.
Tetrahedron Letter, 1977, 23, 1977 by B. Lal, et al.
Synthesis, 1990, 130, by M. C. Viaud, et al.
J. Am. Chem. Soc., 1992, 114, 2741, by C. M. Gasparski.
J. Org. Chem. 1993, 58, 1672, by T. J. Blacklock, et al.
Angew. Chem. Int. Ed. Engl. 1983, 22, 65 by F. Effenberger, et al.
Synthesis 1987, 190, by E. Fabiano, et al.
Tetrahedron 1992, 48, 3007, by R. V. Hoffman.
J. Org. Chem. 1981, 46, 5173, by J. Zaloom, et al.
Fieser and Fieser's Reagents for Organic Synthesis, vol. 8, p. 211, by Mary Fieser, 1980.
Tetrahedron Letters, vol. 30, No. 42, pp. 5709–5712, 1989, by J. R. Henry, et al.
Tetrahedron Letters, vol. 31, No. 24, pp. 3417–3420, 1990, by M. L. Edwards, et al.
J. of Amer. Chem. Society, 97:24, Nov. 26, 1975, by M. Tachikawa, et al.
Biochemistry 1992, 31, 8160–8170, W. B. Knight, et al.
Tetrahedron Letters, 1657, 30, 1989.
Tetrahedron Letters, 7095, 30, 1989.

*Primary Examiner*—Johann Richter
*Assistant Examiner*—Rebecca Cook
*Attorney, Agent, or Firm*—Curtis C. Panzer; David L. Rose; Robert J. North

[57] ABSTRACT

Described is a process for converting an alcohol to an azide with $S_N2$ inversion using a phosphoryl azide, e.g. diphenylphosphoryl azide (DPPA). Good yields of azide in high enantiomeric excess can be achieved specifically for benzylic alcohols and alpha-hydroxy alkyl esters. The process is carried at preferably room temperature in an inert dry aprotic solvent, e.g. toluene, and in the presence of a proton acceptor, e.g. 1,8-diazabicyclo[5.4.0]undec-7-ene (DBU) to afford high yields of high enantiomeric purities.

10 Claims, No Drawings

CONVERTING AN ALCOHOL TO AN AZIDE WITH S$_N$2 INVERSION USING A PHOSPHORYL AZIDE

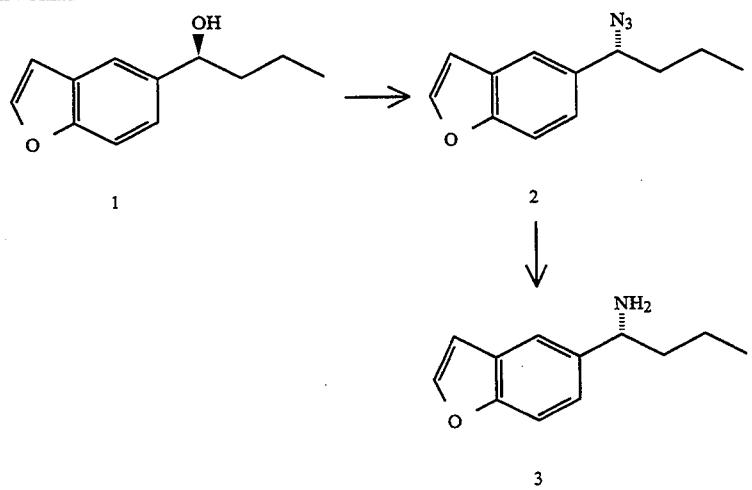

BRIEF DESCRIPTION OF THE BACKGROUND

1. Field of the Invention

This invention relates to a new process for producing azides from the corresponding benzylic alcohols or alpha hydroxy alkane esters with S$_N$2 inversion by the use of a phosphoryl azide and proton acceptor in a suitable solvent.

2. Brief Description of Disclosures in the Field

The synthesis of the orally active elastase inhibitor I below is described in J. Med. Chem. 1992, Vol. 35, p. 3745 by Shah, S. K. et al.:

STRUCTURE

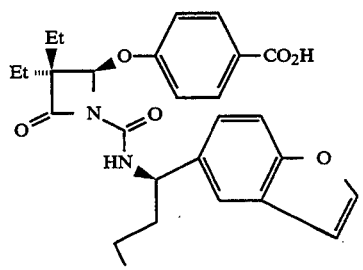

In the process of preparing closely related active derivatives, an enantiomerically pure amine 3 was required which on paper should be able to be produced through the azide 2.

An initial attempt to prepare the amine was made to activate the alcohol 1 by the known process of converting it to a sulfonate derivative and then displacing with an alkali azide. However, these efforts were abandoned because the activated alcohol was decomposing at temperatures far below that required for the displacement step (decomposition was observed at 0° C.).

An examination of the literature provided few methods for alcohol to azide conversions which maintain optical activity with electron rich benzylic alcohols. Use of the Mitsunobu displacement with an azide nucleophile[2] (note: The superscripts refer to literature references listed in the back of the specification) appeared to have the best precedent. Azide can be first introduced under Mitsunobu conditions using hydrazoic acid as the azide source[3] and this method can be extended to chiral α-arylethylamines.[4] Alternatives to the use of hydrazoic acid include diphenyl-phosphoryl azide[5] (DPPA), by Bose et al., and zinc azide/bis pyridine complex.[6]

Applying the conditions of Bose et al.[4] to our substrate undesirably led to elimination product 5 and racemic azide 4, i.e.,

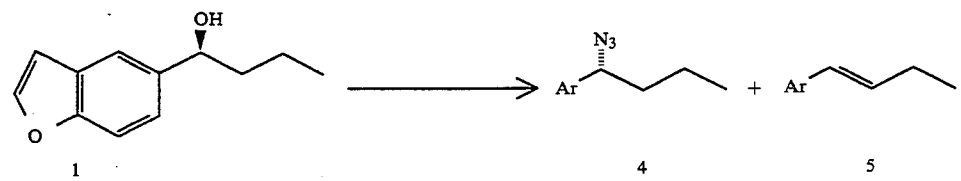

| 1 | | 4 | 5 |
|---|---|---|---|
| 99.6% ee | (PhO)$_2$PON$_3$/DBU} | 91% yield 97% ee | <2% |
| | EtO$_2$CN=NCO$_2$Et  (PhO)$_2$PON$_3$/PPh$_3$ } | 84% yield 82% ee | 6–8% |

In a modification of Bose's procedure the alcohol 1 and triphenylphosphine were added sequentially to a THF solution of diethylazodicarboxylate and DPPA at 0° C. After 30 minutes the product was isolated using an aqueous workup. The azide 4 was isolated in 81% yield with only an optical purity of 82% ee. The reaction also undesirably produced 6–8% of the olefin 5. In addition, the azide was contaminated with 6 times its weight in Mitsunobu by-products so that an extensive chromatography was required, for purification. Undesirable loss of optical activity as well as olefin formation were attributed to highly reactive intermediates which can partition between ionization and displacement chemistry ($S_N1$ vs $S_N2$).

What is desired in the art is a process for converting an alcohol to an azide which undergoes a clean $S_N2$ inversion resulting in a high yield and enantiomeric purity of the azide product.

SUMMARY OF THE INVENTION

We have discovered that the Mitsunobu conditions requiring the use of a dialkyldiazodicarboxylate and triphenylphosphine can be avoided altogether and that the use of diphenyldiphosphorylazide in the presence of an organic proton acceptor directly and unexpectedly affords superior results. The process of converting an alcohol directly to an azide with substantial SN2 conversion in high enantiomeric purity can be carried out by dissolving the alcohol (1 equivalent) and DDPA (1.2 equivalents) in a dry aprotic solvent, e.g., toluene, yielding an alcohol concentration of ca. 0.5–1 molar, and adding a slight equivalent excess of 1,8-diazabicyclo[5.4.0]undec-7-ene (DBU) to the mixture. After stirring at room temperature for several hours the reaction mixture can be simply worked up by an aqueous washing and collecting the product. For example, in the above example, after stirring for about 5 hours at 23° C. the azide 4 was isolated in 91% yield using a simple aqueous workup. The optical purity of the azide was 97% ee (enantiomeric excess of the desired isomer) and there was less than 1% of the elimination product 5.

By this invention there is provided a process for converting an alcohol moiety to the corresponding azide with SN2 inversion comprising the step of:

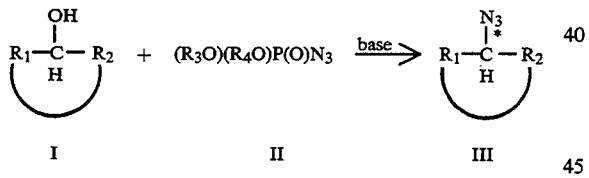

reacting said alcohol (I) with a phosphoryl azide (II) in a dry inert aprotic organic solvent, in the presence of a proton acceptor, soluble in said solvent, at a temperature of about −20 to 100 degrees C., for a sufficient time to produce said azide (III), wherein the inverted carbon resulting from said SN2 inversion is indicated with an asterisk, wherein:

(a) R1 is selected from $C_1$-$C_8$ linear or branched alkyl, 5–10 membered monocyclic or bicyclic fused aromatic or heteroaromatic ring which can independently contain the following ring heteroatoms: 1–4 nitrogens; 1 sulfur; 1 oxygen; 1–2 nitrogens and 1 sulfur; or 1–2 nitrogens and 1 oxygen; wherein said ring can be substituted by 1–3 substituents indicated by X, Y or Z which are independently selected from: hydrogen, halo, trihalo-$C_1$ alkyl, $C_1$-$C_8$ alkyl, $C_1$-$C_8$ alkoxy, NH—CO—$C_1$-$C_8$ alkyl, NH—CO-phenyl, NH—CO—O$C_1$-$C_8$ alkyl, NH—CO-phenyl, N(CO-$C_1$-$C_8$ alkyl)$_2$, N(CO-phenyl)$_2$, O—CO-phenyl, or where X and Y can be 1,2-methylenedioxy, wherein said $C_1$-$C_8$ alkyl or phenyl radicals in said substituents can in turn be substituted by. 1–3 of halo, $C_1$-$C_8$ alkoxy and for phenyl, additionally, $C_1$-$C_8$ alkyl;

(b) R2 is selected from COO$C_1$-$C_8$ alkyl, $C_1$-$C_8$ alkyl, $C_1$-$C_8$ alkylcarbonyl, and where $R_1$ is an aromatic or heteroaromatic ring, $R_2$ can be

where n is 1–5, $R_5$ is hydrogen, $C_1$-$C_8$ alkyl, and wherein $R_2$ can also be a $C_1$-$C_3$ alkylene chain, indicated by the solid curved line, which can contain 1 sulfur or 1 oxygen atom in the chain, joined to said $R_1$ when $R_1$ is a 5–10 membered monocyclic or bicyclic fused aromatic ring in the ortho position of said aromatic ring to said alcohol moiety to form a 5–6 membered non-aromatic fused ring;

(c) R3 and R4 are independently selected from $C_1$-$C_8$ alkyl or phenyl, which can be substituted by 1–3 substituents of $C_1$-$C_8$ alkoxy, halo, trihalo-$C_1$ alkyl, and for phenyl, additionally $C_1$-$C_8$ alkyl;

wherein said process is carried out in the absence of dialkylazadicarboxylate.

Further provided is a compound of the structure:

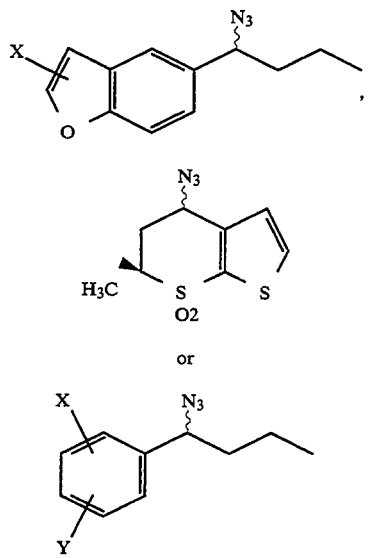

where X and Y are independently are selected from H, p-CF$_3$, p-CH$_3$, m-OCH$_3$, p-OCH$_3$, and X and Y together can represent 1,2-methylenedioxy, wherein the wavy line indicates an alpha or beta bond.

BRIEF DESCRIPTION OF THE INVENTION AND PREFERRED EMBODIMENTS

Mechanistically, the invention process is believed to take place by initially forming a phosphate of the alcohol and liberating the DBU salt of hydrazoic acid. For substrates that are relatively electron deficient this intermediate phosphate has been observed by NMR wherein the benzylic proton of the phosphate is coupled to phosphorus and appears as an apparent quartet at $\delta = 5.5$ ppm for compounds 3 and 4 in Table 1.

The liberated azide salt is similar to a quaternary ammonium azide which has some solubility in organic solvents. This leads to displacement of the sufficiently reactive phosphate leaving group by the organic soluble form of azide at ambient temperatures.

We have discovered that the in-situ generated azide will completely displace the phosphate without the need for any additional azide source, i.e., alkali metal azide, $HN_3$ or sodium azide. Once the azide displacement is complete (benzylic methine at $\delta=4.3$ ppm in compounds 3 and 4), the DBU salt of diphenyl phosphate is formed. This salt is water soluble and can be removed simply with an aqueous wash without the need of an extensive chromatography separation. Any excess DBU can be removed with an acid wash and what is left is the reaction product azide which contains only the slight excess of DPPA initially used. Analytically pure samples of the azide can be then obtained by silica gel chromatography. In addition to the operational simplicity of this reaction, there are far fewer byproducts to contend with than the Mitsunobu reaction, the yield is improved, and the enantiomeric purity of the desired inversion product is maintained.

The yields in the process are in the range of 60 to 95% of theory based on the starting alcohol.

The enantiomeric excess (ee) is the amount of free optically active isomer above the amount present as a racemate. For example a 96% enantiomeric excess (ee) indicates that 2% of each enantiomer is present leaving 96% of the desired pure enantiomer.

The alcohol in the process undergoes a SN2 reaction in which the carbon attached to the alcohol becomes inverted in the resulting azide. Thus, an alpha alcohol will result in a beta azide, and beta alcohol will result in an alpha azide.

The alcohol useful in the process is of the structure:

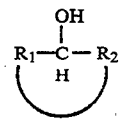

wherein $R_1$ and $R_2$ are defined above.

By the term $C_1$-$C_8$ alkyl as used herein includes linear or branched alkyls including: methyl, ethyl, propyl, isopropyl, n-butyl, isobutyl, sec-butyl, t-butyl, pentyl, hexyl, isohexyl, heptyl, octyl, isooctyl, and the like. Preferred is methyl.

By the term "$C_1$-$C_8$ alkoxy" as used herein includes the $C_1$-$C_8$ alkyl radical discussed above attached to an ether radical and includes: methoxy, ethoxy, propoxy, isopropoxy, n-butoxy, isobutoxy, sec-butoxy, t-butoxy, pentoxy, hexoxy, isohexoxy, heptoxy, octyloxy, isooctyloxy, and the like. Preferred is methoxy.

By the term "halo" as used herein is meant fluoro, chloro or bromo. Preferred is fluoro.

The monocyclic or bicyclic fused aromatic/heteroaromatic rings which are operative in the instant invention include: phenyl, naphthyl, pyridyl, pyrryl, furyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, benzthiazolyl, benzoxazolyl, thiazolyl, oxazolyl, and 1,4-benzodiazepinyl, wherein the NH moiety of the indolyl, isoindolyl, carbazolyl or benzodiazepinyl group is protected by a removable $C_1$-$C_4$ alkanoyl group, e.g. acetyl, during the process. The alkanoyl group can be easily removed by conventional mild alkaline hydrolysis e.g., by contacting with sodium hydroxide solution.

Preferred aromatic/heteroaromatic rings include phenyl, naphthyl, furyl, thiophenyl, benzothienyl, benzofuryl.

Preferably the alcohol (I) is selected from:

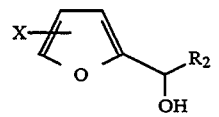

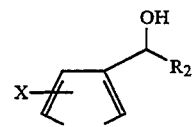

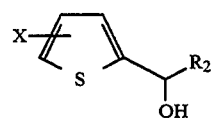

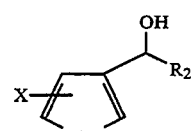

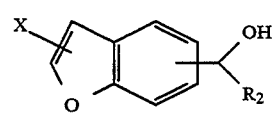

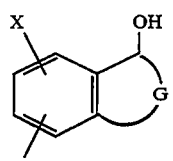

wherein G is C2-C4 alkylene, which can be substituted with a C1-C3 alkyl and said alkylene chain can contain a $S(O)_n$ ring atom, where n is 0-2;

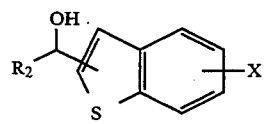

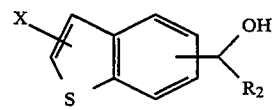

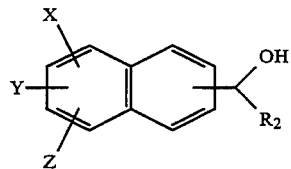

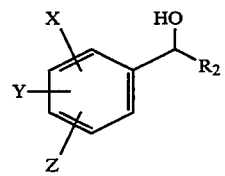

-continued

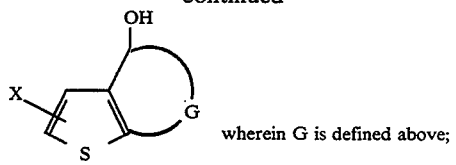 wherein G is defined above;

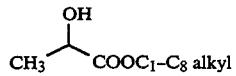

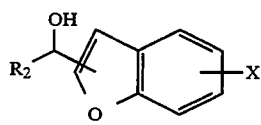

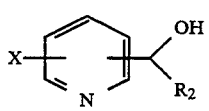

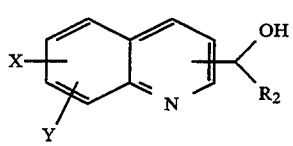

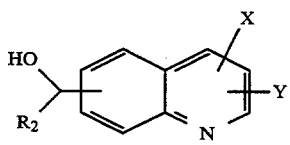

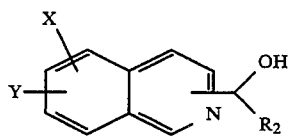

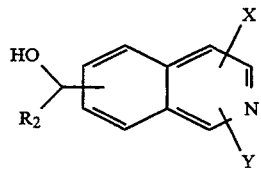

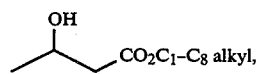

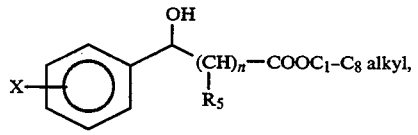

resulting in the corresponding azide product (III) having an inverted azide carbon atom.

Particularly preferred is where the alcohol is selected from:

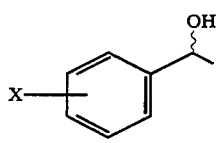 where X is H, p-CF₃, p-CH₃, m-OCH₃, p-OCH₃, and the wavy line can be an alpha or beta bond -continued

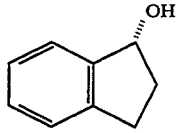

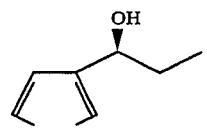

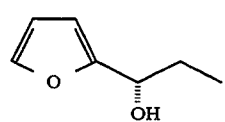

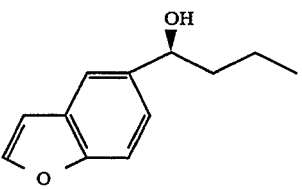

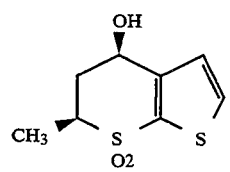

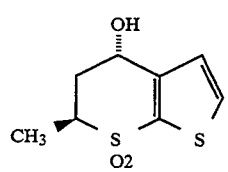

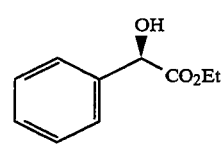

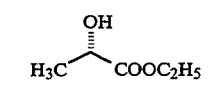

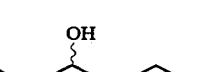

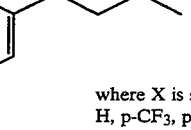

where X is selected from H, p-CF₃, p-CH₃, m-OCH₃, p-OCH₃, and X and Y together can represent 1,2-methylenedioxy, and wherein the wavy line can be either an alpha or beta bond and said corresponding inverted azide is:

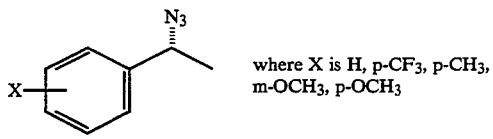
where X is H, p-CF$_3$, p-CH$_3$, m-OCH$_3$, p-OCH$_3$

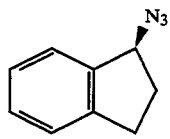

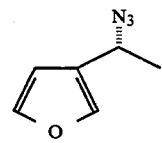

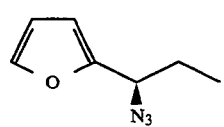

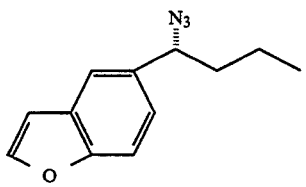

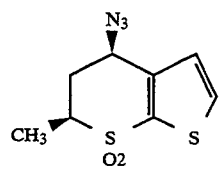

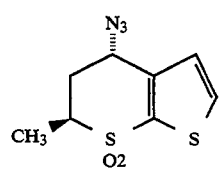

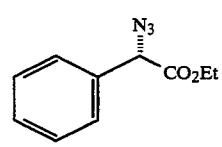

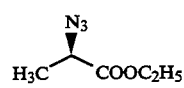

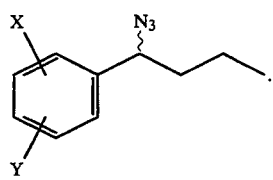

Also a subject of this invention are the following new compounds:

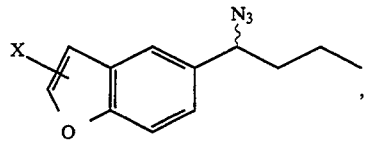

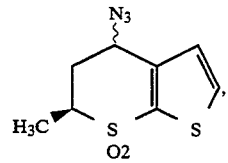

or

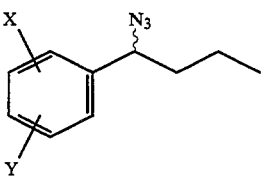

where X and Y are independently are selected from H, p-CF$_3$, p-CH$_3$, m-OCH$_3$, p-OCH$_3$, and X and Y together can represent 1,2-methylenedioxy wherein the wavy line indicates an alpha or beta bond.

The phosphoryl azide utilized in the process is of the formula:

$$(R_3O)(R_4O)P(O)N_3$$

wherein:

$R_3$ and $R_4$ are independently selected from $C_1$-$C_8$ alkyl or phenyl, which can be substituted by 1-3 substituents of $C_1$-$C_8$ alkoxy, halo, trihalo-$C_1$ alkyl, and for phenyl, additionally $C_1$-$C_8$ alkyl. Preferably, $R_3$ and $R_4$ are both phenyl.

The phosphoryl azides encompassed by the above description are either known in the art or can be made by analogous procedures to those described in the art.

Representative phosphoryl azides include:

diphenyl phosphoryl azide
di(p-methoxyphenyl)phosphoryl azide
di(p-fluorophenyl)phosphoryl azide
di(p-tolyl)phosphoryl azide
diethyl phosphoryl azide
di(n-butyl)phosphoryl azide
di(p-CF$_3$ phenyl)phosphoryl azide
di(2,4-dichlorophenyl)phosphoryl azide
and the like. Preferred is diphenylphosphorylazide.

The proton acceptor useful in the process include: $C_6$-$C_{10}$ diazabicycloalkanes, $C_6$-$C_{10}$ diazabicycloalkenes, 1-5 $C_1$-$C_3$ alkyl substituted guanidines, $C_4$-$C_9$ heteroaromatic N-containing compounds, or mono or di-$C_1$-$C_4$ alkylamino substituted pyridines. All of these proton acceptors are known in the art or can be made by analogous procedures according to the art.

Representative examples are:

1,8-diazabicyclo[5.4.0]undec-7-ene (DBU)
1,4-diazabicyclo[2.2.0]octane (Dabco)
1,5-diazabicyclo[4.3.0]non-5-ene (DBN)
1,1-dimethylguanidine
1,1,3,3-tetramethylguanidine 1,1,3,3,4-pentamethylguanidine
pyridine
quinoline
4-(dimethylamino)pyridine
4-(diethylamino)pyridine.
Preferred are DBU and Dabco.

Temperature in the process is carried out in the range of −20 to 100 degrees C. preferably in the range of 20 to 50 degrees C. and particularly preferred at room temperature.

The solvent useful in the process is a dry, inert, aprotic solvent for the alcohol, phosphoryl azide and proton acceptor. The useful solvents include $C_5-C_{12}$ saturated hydrocarbons, $C_6-C_{10}$ aromatic hydrocarbons, which can be substituted with 1-3 halo (Br, Cl, F) or $C_1-C_4$ alkyl substituents, 1-4 halogenated $C_1-C_6$ linear or cyclic alkane, $C_4-C_6$ linear or cyclic ether, $C_1-C_2$ N,N-dialkylformamide, $C_1-C_2$ N,N-dialkylacetamide or $C_1-C_2$ alkylnitrile.

These solvents are commercially available and include: hexane, benzene, toluene, m-xylene, p-xylene. naphthalene, chlorobenzene, o-dichlorobenzene, methylene chloride, chloroform, carbon tetrachloride, chlorocyclohexane, diethyl ether, dioxane, tetrahydrofuran (THF), 1,2-dimethoxyethane, N,N-dimethylformamide, N,N-diethylformamide, N,N-dimethylacetamide, N,N-diethylacetamide, acetonitrile and the like. Preferred are THF and toluene.

The process is carried out preferably under a dry inert atmosphere, including dry nitrogen. Conventional apparatus is used.

The following examples illustrate the gist of the invention and should not be construed as being limitations on the scope and/or spirit of the instant invention.

EXAMPLES

The general azidation procedure used in the examples is as follows:

General Procedure

The alcohol (1 mmol) and diphenylphosphoryl azide (1.2 mmol) are dissolved in dry solvent (toluene or THF) (2 ml). To the mixture under $N_2$ is added neat 1,8-diazabicyclo[5.4.0]undec-7-ene (1.2 mmol). The reaction is stirred at 20 degrees C. until complete, typically in 12 hours. The mixture is diluted with toluene (3 ml) and washed with water (2×3 ml) and 5% HCl (3 ml). The organic layer is concentrated in vacuo and purified using silica gel chromatography to afford pure azide with a typical yield of 80–95% and a typical enantiomeric excess of about 80 to 99%. The general procedure is shown mechanistically below, for 1-aryl (Ar)-1-hydroxy propane-benzylic type alcohols.

We have extended this reaction to a variety of structurally diverse alcohols shown in Table 1. The examples shown as Compounds 1-5 span a range from electron deficient (para-CF3) to electron rich benzylic alcohols (para OMe). A benzylic alcohol attached to a metamethoxy substituted phenyl group (Compound 3) was recently used in conjunction with the Mitsunobu displacement to demonstrate a chiral amine synthesis.[4] However, the meta-methoxy substituent is in fact electron withdrawing (positive Hammett $\sigma$ value) and less prone to racemization than is an unsubstituted phenyl.[8] We have demonstrated the method using a more general class of benzylic alcohols. It is clear that the substrates need not be electron rich for a successful conversion. However, variations in the electronic nature of substituents on the aryl ring affect the rate of the displacement step. In all cases the phosphate was formed within an hour, however, Compound 2 (para-CF3) required warming to 40° C. to complete the displacement, while Compound 5 (para-OMe) was complete in several hours at 0° C. Compounds 7 through 9 show the extension to electron rich heterocycles. Racemization was typically less than 2% for all examples except for the para methoxyphenyl (Compound 5) and the 2-substituted furan (Compound 8). In these two examples there was 5% and 10% of the opposite enantiomer produced, respectively. Compounds 10 and 11 demonstrate the method using different intermediates.9 The C-4 cis and trans alcohols both undergo complete inversion. That both diastereomers invert rules out the possibility of an $\alpha$ face selective attack of azide.[9] Currently this is the highest level of stereocontrol reported for introducing the C-4 amine into these type of molecules. The method can be extended to afford protected amino acids (Compound 12). In this case, the ester sufficiently activates the hydroxyl for displacement without an adjacent phenyl ring.[10,11] Since the products are prone to epimerization[10b] a slight undercharge of base was used (0.98 equivalents).

The primary alcohol in Compound 13 formed an azide very slowly in toluene or THF at ambient temperature (5% conversion after 24 h). Use of conditions more favorable for an $S_N2$ displacement led to complete azide formation (DMF at 65° C. for 3 h).[12] A secondary alcohol formed an azide in low yield even under forcing conditions (Compound 14; DMF at 125° C. for 18 h). However, this substrate forms an azide in good yield using the Mitsunobu conditions.[5] This observation allows for a ranking of the relative reactivities using Mitsunobu conditions compared with our method. In the Mitsunobu reaction, the reactive intermediate is proposed to be an alkoxy phosphonium species.[2b] This highly reactive intermediate readily allows unactivated secondary alcohols to be displaced. Such highly reactive intermediates can be undesirable when an optically active electron rich benzylic alcohol is the substrate. In this case, the phosphate has the appropriate balance of reactivity such that racemization is suppressed yet the displacement with azide is facile at temperatures between 0°-25° C.

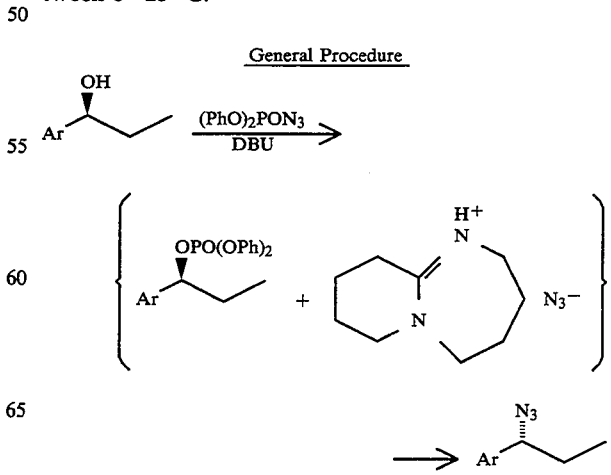

General Procedure

TABLE 1

| Compound | ALCOHOL[a] | AZIDE[b] | YIELD |
|---|---|---|---|
| 1 | X = H[d] 99% ee | 98.7% ee | 93% |
| 2 | X = CF₃[c] 95.2% ee | 94.3% ee | 94% |
| 3 | X = meta-OMe[3] 97.5% ee | 96.0% ee | 89% |
| 4 | X = para-CH3[e] 97% ee | 95% ee | 91% |
| 5 | X = para-OMe[e] 99.4[f]% ee | 87.6% ee | 80% |
| 6 | 99.5% ee[c] | 94.1% ee | 95% |
| 7 | 97.4% ee[e] | 96.9% ee | 82% |
| 8 | 92.5% ee[e] | 71.3% ee | 86% |
| 9 | 99.6% ee[e,g] | 97.5% ee[b] | 90% |
| 10 | 95:5[h] cis:trans | 5:95[h,i] cis:trans | 92% |
| 11 | 2:98[h] cis:trans | 97:2[h,i] cis:trans | 92% |
| 12 | | | 87% |

TABLE 1-continued

| Compound | ALCOHOL[a] | AZIDE[b] | YIELD |
|---|---|---|---|
|  | 99% ee[j] | 98% ee[i,k] |  |
| 13 | n-decanol | n-decyl azide | 88% |
| 14 | cholesterol | cholesteryl azide | 20% |

(a) The optical purity was determined by gas chromatography using a Cyclodex-B column. (b) The ratio of enantiomers was determined by reverse phase HPLC after reducing the azide to the amine with LiAlH$_4$ and converting the amine to the menthyl carbamate (-menthyl chloroformate, triethylamine). All examples were compared to independently prepared racemic samples. (c) The alcohol was prepared via an enantioselective ketone reduction, reference 13. (d) The alcohol was purchased from Aldrich. (e) The alcohol was prepared via an asymmetric dialkylzinc addition according to the procedure outlined in reference 14. (f) The optical purity was determined using a chiralcel OD column. (g) The optical purity was determined using a chiralcel OB column. (h) The alcohol ratio was determined by reverse phase HPLC, and the azide ratio was determined by $^1$H NMR. (i) The azidation was nm in THF. (j) The optical purity was taken as the chemical purity from Aldrich. (k) The ratio of enantiomers was determined using a chiracel crownpak (CR+) column after reducing the azide to the amine with triphenylphosphine.

REFERENCES and FOOTNOTES

1. Shah, S. K.; Dorn, C. P.; Finke, P. E.; Hale, J. J.; Hagman, W. K.; Brause, K. A.; Chandler, G. O.; Kissinger, A. L.; Ashe, B. M.; Weston, H.; Knight, W. B.; Maycock, A. L.; Dellea, P. S.; Flecher, D. S.; Hand, K. M.; Mumford, R. A.; Underwood, D. J.; Doherty, J. B. *J. Med. Chem.* 1992, 35, 3745.
2. (a) The first example in which an amine equivalent was installed under Mitsunobu conditions used phthalimide: Mitsunobu, O.; Wada, M.; Sano, T. *J. Am. Chem. Soc.* 1972, 94, 679. (b) The Mitsunobu displacement has been extensively reviewed by Hughes. References to the variation in which a C-N bond is formed can be found in this review, see; Hughes, D. L. *Org. React.* 1992, 42, 335.
3. Loibner, H.; Zbiral, E. *Helvetica Chimica Acta*, 1977, 60, 417.
4. Chen, C.-P.; Prasad, K.; Repic, O. *Tetrahedron Lett*, 1991, 32, 7175.
5. Lal, B.; Pramanik, B. N.; Manhas, M. S.; Bose, A. K. *Tetrahedron Lett*, 1977, 1977.
6. Viaud, M. C.; Rollin, P. *Synthesis*, 1990, 130.
7. A similar observation was made in the β-lactam area, see: Gasparski, C. M.; Teng, M.; Miller, M. J. *J. Am. Chem. Soc.* 1992, 114, 2741.
8. Lowry, T. M.; Richardson, K. S. "Mechanism and Theory in Organic Chemistry"; 2nd Ed. Harper and Row, 1981, p. 134.
9. Blacklock, T. J.; Sohar, S.; Butcher, J. W.; Lamanec, T.; Grabowski, E. J. J. *J. Org. Chem.* 1993, 58, 1672.
10. For an example of displacing an α-hydroxy ester with an amine equivalent see: (a) Displacement of a trifluoromethanesulfonate: Effenberger, F.; Burkard, U.; Willfahrt, *J. Angew. Chem. Int. Ed. Engl.* 1983, 22, 65. (b) For an example using the Mitsunobu displacement with HN$_3$ see: Fabiano, E.; Golding, B. T.; Sadeghi, M. M. *Synthesis* 1987, 190. (c) For an example using a protected hydroxylamine under Mitsunobu conditions see: Kolasa, T.; Miller, M. J. *J. Org. Chem.* 1987, 52, 4978. (d) For an example using a p-nitrobenzenesulfonate, see: Hoffman, R. V.; Kim, H. -O. *Tetrahedron* 1992, 48, 3007.
11. For the preparation of azido derivatives of amino acids by diazo transfer, see: Zaloom, J.; Roberts, D. C. *J. Org. Chem.* 1981, 46, 5173.
12. We have observed gas evolution when DPPA and DBU were mixed in polar solvents such as CH$_3$CN or DMF without the alcohol present. The base should always be added last.
13. Mathre, D. J.; Thompson, A. S.; Douglas, A. W.; Hoogsteen, K.; Carroll, J. D.; Corley, E. G.; Grabowsli, E. J. J. *J. Org. Chem.*, 1993, 58, 2880.
14. Yoshioka, M.; Kawakita, T.; Ohno, M., *Tetrahedron Lett*, 1989, 30, 1657. Takahashi, H.; Kawakita, T.; Yoshioka, M.; Kobayashi, S.; Ohno, M., ibid, 1989, 30, 7095.
15. The boiling points (melting point) and rotations for the azides in Table 1 are as follows, Compound, Bp, rotation: 1, 65° C./0.5 mm, $[\alpha]D^{25}=-69.4$ (c=1.02, hexane); 2, 105°–110° C./15 mm, $[\alpha]D^{25}=-115.1$ (c=1.02, hexane); 3, 95° C./1 mm, $[\alpha]D^{25}=+155.5$ (c=1.0, hexane); 4, $[\alpha]D^{25}=+170.5$ (c=1.0, hexane); 5, 110° C./0.6 mm, $[\alpha]D^{22}=+141.2$ (c=0.99, hexane); 6, 140° C./15 mm; $[\alpha]D^{23}=-25.3$ (c=1.1 hexane); 7, 100° C./30 mm, $[\alpha]D^{25}=+99.2$ (c=1.0, hexane); 8, 105° C./35 mm, $[\alpha]D^{25}=+96.7$ (c=1.0 hexane); 9, $[\alpha]D^{25}=-125$ (c=1.02, hexane); 10, mp=118°–119° C., $[\alpha]D^{25}=-232$ (c=1.13, MeOH); 11, mp=99°–101° C., $[\alpha]D^{25}=-53.9$ (c=1.02, MeOH); 12, 105°–110° C./100 mm, $[\alpha]D^{25}=+17.5$ (c=1.03, hexane).

What is claimed is:

1. A process for converting an alcohol moiety to the corresponding azide with SN$_2$ inversion comprising the step of:

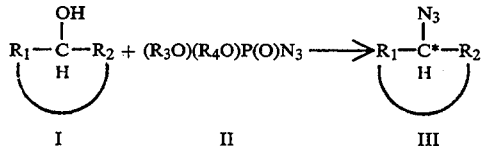

reacting said alcohol (I) with a phosphoryl azide (II) in a dry inert aprotic organic solvent in the presence of a proton acceptor, soluble in said solvent, at a temperature of about −20 to 100 degrees C., for a sufficient time to produce said azide (III), wherein the inverted carbon resulting from said SN$_2$ inversion is indicated with an asterisk, wherein:

(a) R$_1$ is selected from the group consisting of C$_1$–C$_8$ linear or branched alkyl, 5–10 membered monocyclic or bicyclic fused aromatic or heteroaromatic ring, wherein the hetero ring atoms are independently selected from the group consisting of nitrogen, sulfur and oxygen; wherein said aromatic or heteroaromatic ring can be substituted by 1-3 substituents X, Y or Z said substituents being independently selected from the group consisting of halo, trihalo-$C_1$ alkyl, $C_1$-$C_8$ alkyl, $C_1$-$C_8$ alkoxy, NH—CO-$C_1$-$C_8$ alkyl, NH—CO-phenyl, NH—CO—O$C_1$-$C_8$ alkyl, N(CO-$C_1$-$C_8$ alkyl)$_2$, N(CO-phenyl)$_2$, O—CO-phenyl, or X and Y may be 1,2-methylenedioxy, without affecting the value of Z, wherein the $C_1$-$C_8$ alkyl or phenyl moieties in said X, Y or Z substituents can in turn be substituted by 1-3 substituents independently selected from the group consisting of halo, $C_1$-$C_8$ alkoxy and for phenyl, additionally the substituents can be, $C_1$-$C_8$ alkyl;

(b) $R_2$ is selected from
 (i) —COO$C_1$-$C_8$ alkyl, $C_1$-$C_8$ alkyl, $C_1$-$C_8$ alkylcarbonyl;
 (ii) where $R_1$ is an aromatic or heteroaromatic ring, $R_2$ may further be

where n is 1-5, $R_5$ is hydrogen or $C_1$-$C_8$ alkyl, or $R_1$ and $R_2$ are joined, such that together with the atoms to which they are attached there is formed a compound of the formula

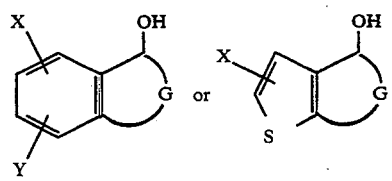

wherein G is $C_2$-$C_4$ alkylene, which can be substituted with a $C_1$-$C_3$ alkyl and said alkylene chain can contain a $S(O)_n$ ring atom, where n is 0-2;

(c) $R_3$ and $R_4$ are independently selected from $C_1$-$C_8$ alkyl or phenyl, which can be substituted by 1-3 substituents of $C_1$-$C_8$ alkoxy, halo, trihalo- $C_1$ alkyl, and for phenyl, additionally $C_1$-$C_8$ alkyl;
wherein said process is carried out in the absence of dialkylazadicarboxylate.

2. The process of claim 1 wherein $R_3$ and $R_4$ are both phenyl.

3. The process of claim 1 wherein said temperature is in the range of 20-50 degrees C.

4. The process of claim 1 wherein said proton acceptor is a $C_6$ to $C_{10}$ diazabicycloalkane or alkene, 1-5 $C_1$-$C_3$ alkyl substituted guanidine, $C_4$-$C_9$ heteroaromatic nitrogen compound, or mono or di $C_1$-$C_4$ alkylamino substituted pyridine.

5. The process of claim 1 wherein said solvent is a $C_5$-$C_{12}$ saturated hydrocarbon, $C_6$-$C_{10}$ aromatic hydrocarbon, which can be substituted with 1-3 halo or $C_1$-$C_4$ alkyl substituents, 1-4 halogenated $C_1$-$C_6$ alkane, $C_4$-$C_6$ linear or cyclic ether, N,N-di-$C_1$-$C_2$ alkylformamide, N,N-di-$C_1$-$C_2$ alkylacetamide, or $C_1$-$C_2$ alkyl nitrile.

6. The process of claim 1 wherein R1 is an aromatic or heteroaromatic ring selected from the group consisting of phenyl, naphthyl, pyridyl, pyrryl, furyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, benzthiazolyl, benzoxazolyl, thiazolyl, oxazolyl, and 1,4-benzodiazepinyl, wherein the NH moiety of the indolyl, isoindolyl, carbazolyl or benzodiazepinyl group is protected by a removable $C_1$-$C_4$ alkanoyl group.

7. The process of claim 1 wherein said alcohol (I) is selected from:

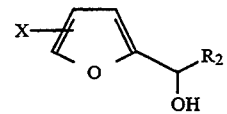

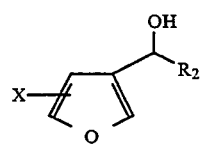

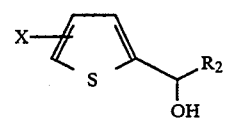

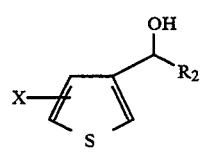

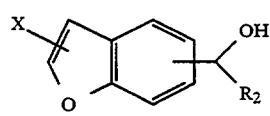

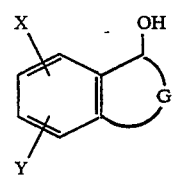

wherein G is $C_2$-$C_4$ alkylene, which can be substituted with a $C_1$-$C_3$ alkyl and said alkylene chain may contain a $S(O)_n$ ring atom, where n is 0-2;

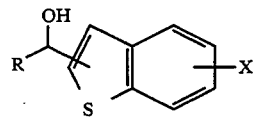

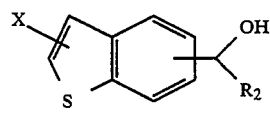

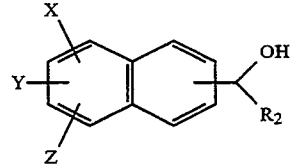

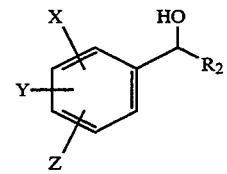

-continued
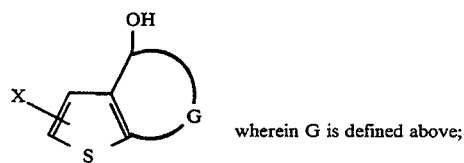
wherein G is defined above;
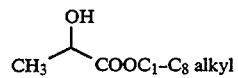
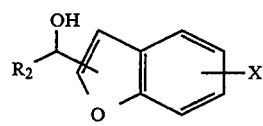
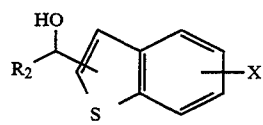
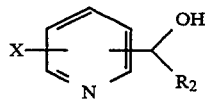
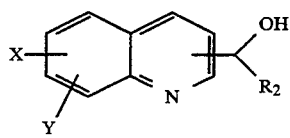
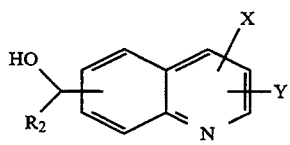
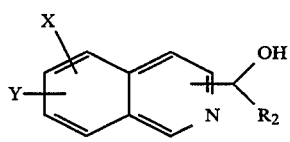
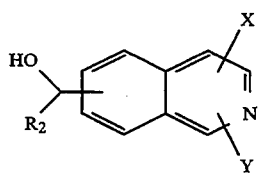
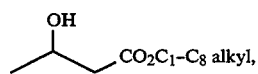
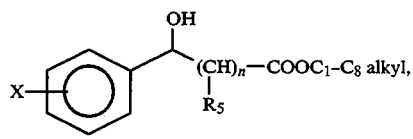
resulting in the corresponding azide product (III) having an inverted azide carbon atom.
8. The process of claim 1 wherein said alcohol I is selected from:
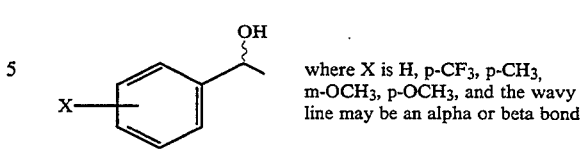
where X is H, p-CF$_3$, p-CH$_3$, m-OCH$_3$, p-OCH$_3$, and the wavy line may be an alpha or beta bond
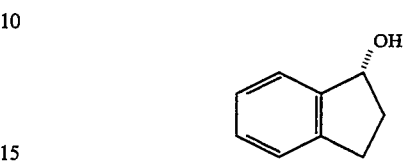
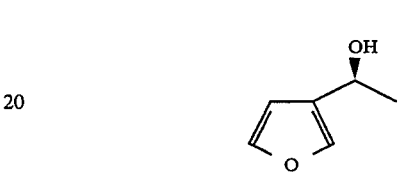
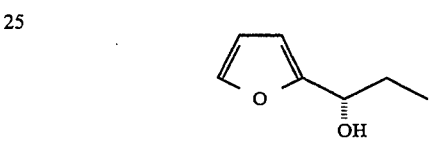
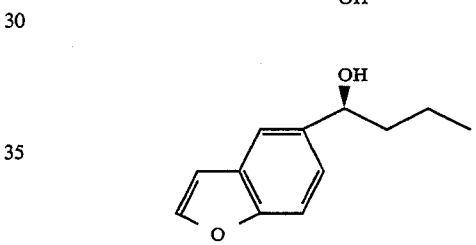
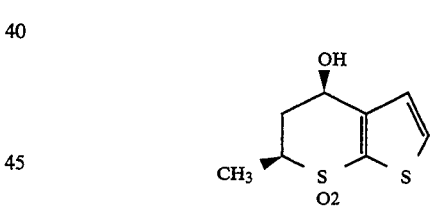
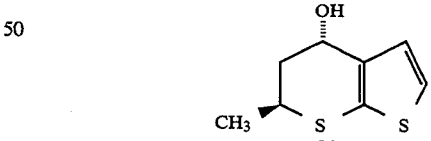
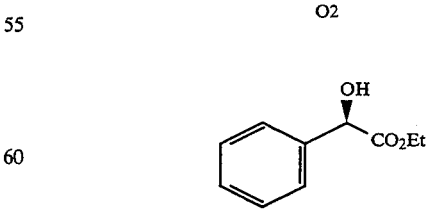
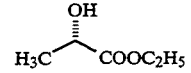

-continued

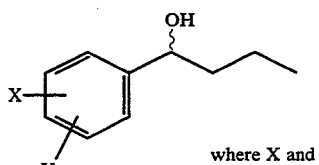

where X and Y are independently selected from H, p-CF$_3$, p-CH$_3$, m-OCH$_3$, p-OCH$_3$, and X and Y together may represent 1,2-methylenedioxy, and wherein the wavy line may be either an alpha or beta bond and said corresponding inverted azide is:

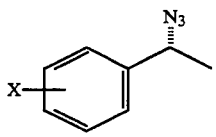

where X is H, p-CF$_3$, p-CH$_3$, m-OCH$_3$, p-OCH$_3$

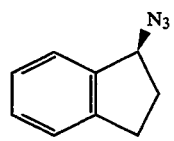

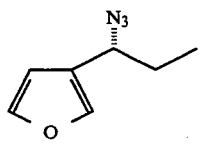

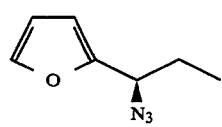

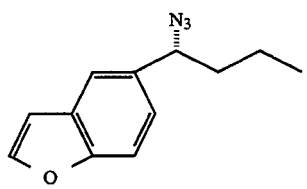

-continued

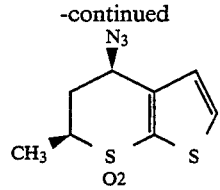

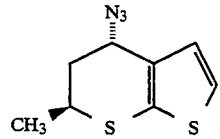

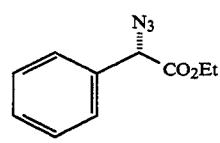

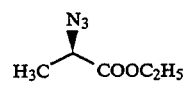

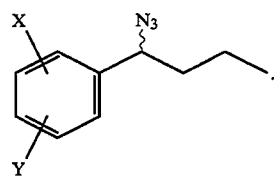

9. The process of claim 1 for converting an alcohol moiety to the corresponding azide with SN$_2$ inversion wherein Structures I and III have the following formulas:

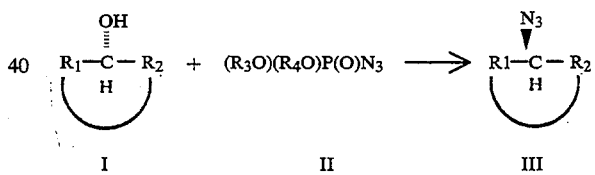

10. The process of claim 1 for converting an alcohol moiety to the corresponding azide with SN$_2$ inversion wherein Structures I and III have the following formulas:

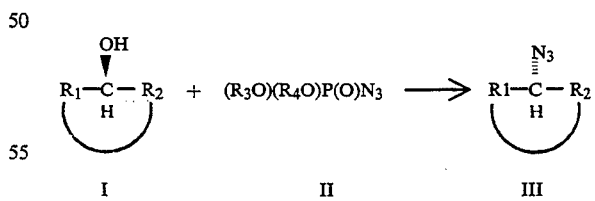

* * * * *